US012741995B2

(12) United States Patent
Glenn et al.

(10) Patent No.: US 12,741,995 B2
(45) **Date of Patent: *Sep. 22, 2026**

(54) UBIQUITIN VARIANT WITH HIGH AFFINITY FOR BINDING 53BP1 REDUCES THE AMOUNT OF AAV NEEDED TO ACHIEVE HIGH RATES OF HDR

(71) Applicant: Integrated DNA Technologies, Inc., Coralville, IA (US)

(72) Inventors: Steve Ehren Glenn, North Liberty, IA (US); Michael Allen Collingwood, Solon, IA (US); Christopher Anthony Vakulskas, North Liberty, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 481 days.

This patent is subject to a terminal disclaimer.

(21) Appl. No.: 18/450,149

(22) Filed: Aug. 15, 2023

(65) Prior Publication Data

US 2024/0059747 A1 Feb. 22, 2024

Related U.S. Application Data

(60) Provisional application No. 63/399,452, filed on Aug. 19, 2022.

(51) Int. Cl.

| | |
|---|---|
| ***C07K 14/47*** | (2006.01) |
| ***C12N 15/86*** | (2006.01) |
| ***C12N 15/90*** | (2006.01) |

(52) U.S. Cl.

CPC .............. *C07K 14/47* (2013.01); *C12N 15/86* (2013.01); *C12N 15/907* (2013.01); *C12N 2750/14143* (2013.01)

(58) Field of Classification Search

CPC ................ C07K 14/47; C07K 14/4703; C07K 14/4702; C07K 2319/00; C07K 2319/10; C07K 2319/95; C12N 15/86; C12N 15/907; C12N 15/102; C12N 2750/14143; C12N 2310/20

See application file for complete search history.

(56) References Cited

FOREIGN PATENT DOCUMENTS

| | | | |
|---|---|---|---|
| CN | 110041424 | A | 7/2019 |
| WO | 2017132746 | A1 | 8/2017 |
| WO | 2022115878 | A1 | 6/2022 |
| WO | 2023049421 | A2 | 3/2023 |

OTHER PUBLICATIONS

Presnell SR, Benner SA. The design of synthetic genes. Nucleic Acids Res. Mar. 11, 1988;16(5):1693-702. (Year: 1988).*

Dan Wang, Feng Zhang, Guangping Gao, CRISPR-Based Therapeutic Genome Editing: Strategies and In Vivo Delivery by AAV Vectors, Cell, vol. 181, Issue 1, (Year: 2020).*

Canny, M. et al.: "Inhibition of 53BP1 favors homology-dependent DNA repair and increases CRISPR-Cas9 genome-editing efficiency", Nature Biotechnology, vol. 36, No. 1, Nov. 27, 2017 (Nov. 27, 2017), pp. 95-102, XP055487471.

International Search Report issued in PCT Patent Application No. PCT/US2023/072220, dated Nov. 23, 2023.

Written Opinion issued in PCT Patent Application No. PCT/US2023/072220, dated Nov. 23, 2023.

* cited by examiner

*Primary Examiner* — Thomas J. Visone
*Assistant Examiner* — Cassandra Senn Grizer
(74) *Attorney, Agent, or Firm* — Potomac Law Group, PLLC; Reza Mollaaghababa; Joseph F. Murphy

(57) ABSTRACT

The present invention pertains to a tag-free CM1 polypeptide and methods for improving homology directed repair (HDR) in a recipient cell using the same. Preferred donor template delivery vehicles include Adeno virus-associated vectors for delivering donor templates, and a preferred tag-free CM1 polypeptide called CM1tf. Isolated nucleic acids encoding tag-free CM1 polypeptides are also provided.

7 Claims, 7 Drawing Sheets

Specification includes a Sequence Listing.

```
                              SEQUENCE LISTING

Sequence total quantity: 40
SEQ ID NO: 1            moltype = AA  length = 85
FEATURE                 Location/Qualifiers
source                  1..85
                        mol_type = protein
                        organism = synthetic construct
SEQUENCE: 1
MHHHHHHGGS GMLIFVKTLT GKTITLEVEP SDTIENVKAK IQDKEGIPPD QQRLAFAGKS  60
LEDGRTLSDY NILKDSKLHP LLRLR                                        85

SEQ ID NO: 2            moltype = AA  length = 85
FEATURE                 Location/Qualifiers
source                  1..85
                        mol_type = protein
                        organism = synthetic construct
SEQUENCE: 2
MHHHHHHGGS GMLIFVRMLT GKMIELEVEP SDTIENVKAK IQDHEGIPPD QQRLAFQGKS  60
LEDGRTLSDY NILKDPKKMP LLRLR                                        85

SEQ ID NO: 3            moltype = AA  length = 74
FEATURE                 Location/Qualifiers
source                  1..74
                        mol_type = protein
                        organism = synthetic construct
SEQUENCE: 3
MLIFVRMLTG KMIELEVEPS DTIENVKAKI QDHEGIPPDQ QRLAFQGKSL EDGRTLSDYN  60
ILKDPKKMPL LRLR                                                    74

SEQ ID NO: 4            moltype = DNA  length = 255
FEATURE                 Location/Qualifiers
source                  1..255
                        mol_type = other DNA
                        organism = synthetic construct
SEQUENCE: 4
atgcaccatc accaccacca cggtggatct ggcatgttga ttttcgtaaa gacgttgact  60
ggaaagacta tcactttgga agtggagcct tccgatacta tcgagaatgt taaggccaaa  120
atccaagata aggaagggat tcctccagat caacaacgcc ttgcttttgc cgggaagagc  180
ctggaggacg gtcgcacact gtctgactat aacattctta aagattctaa attgcatcca  240
ctgctgcgct tgcgt                                                   255

SEQ ID NO: 5            moltype = DNA  length = 255
FEATURE                 Location/Qualifiers
source                  1..255
                        mol_type = other DNA
                        organism = synthetic construct
SEQUENCE: 5
atgcaccacc accaccacca cggtggatct ggcatgttga ttttcgtacg catgttgact  60
ggaaagatga tcgagttgga agtggagcct tccgatacta tcgagaatgt taaggccaaa  120
atccaagatc atgaagggat tcctccagat caacaacgcc ttgcttttca agggaagagc  180
ctggaggacg gtcgcacact gtctgactat aacattctta aagatcctaa aaagatgcca  240
ctgctgcgct tgcgt                                                   255
```

```
SEQ ID NO: 6            moltype = DNA  length = 222
FEATURE                 Location/Qualifiers
source                  1..222
                        mol_type = other DNA
                        organism = synthetic construct
SEQUENCE: 6
atgttgattt tcgtacgcat gttgactgga aagatgatcg agttggaagt ggagccttcc  60
gatactatcg agaatgttaa ggccaaaatc caagatcatg aagggattcc tccagatcaa  120
caacgccttg cttttcaagg gaagagcctg gaggacggtc gcacactgtc tgactataac  180
attcttaaag atcctaaaaa gatgccactg ctgcgcttgc gt                     222

SEQ ID NO: 7            moltype = DNA  length = 20
FEATURE                 Location/Qualifiers
source                  1..20
                        mol_type = other DNA
                        organism = synthetic construct
SEQUENCE: 7
acctctggaa aaaggtaaga                                              20

SEQ ID NO: 8            moltype = DNA  length = 20
FEATURE                 Location/Qualifiers
source                  1..20
                        mol_type = other DNA
                        organism = synthetic construct
SEQUENCE: 8
aattatgggg attactagga                                              20

SEQ ID NO: 9            moltype = DNA  length = 20
FEATURE                 Location/Qualifiers
source                  1..20
                        mol_type = other DNA
                        organism = synthetic construct
SEQUENCE: 9
cttggattga gagtcaagat                                              20

SEQ ID NO: 10           moltype = DNA  length = 1006
FEATURE                 Location/Qualifiers
source                  1..1006
                        mol_type = other DNA
                        organism = synthetic construct
SEQUENCE: 10
cttgtccctc tttgccttct ctaattagat atttctctct ctctctccct ctctccataa  60
agaaaactat gagagagggt gggtatgaac caagtttgtt tccttggtta gtttcctaac  120
caagtttgag ggtatgaaca tactctcctt ttccttttct ataaagctga ggagaagagt  180
gagggagtgt gggcaagaga ggtggctcag gctttccctg ggcctgattg aactttaaaa  240
cttctctact aattaaacaa cactgggctc tacactttgc ttaaccctgg gaactggtca  300
tcagcctttg acctcagttc cccctcctga ccagctctct gccccaccct gtcctctgga  360
acctctgcga gatttagagg aaagaaccag ttttcaggcg gattgcctca gatcacacta  420
tctccacttg cccagccctg tggaagatta gcggccatgt attccaatgt gataggaact  480
gtaacctctg gaaaaaggta gaattcagag gggtgagctt tcccccttgcc tgcccctact  540
gggttttgtg acctccaaag gactcacagg aatgacctcc aacacctttg agaagaccag  600
gccctctccc tggtagttac agtcaaagac ctgtttggaa gacgtcattt caagtgctct  660
ccctcccacc ccacctcttg gggtaaggcc tttcctaagc taccccttgg gtccctagcc  720
taagaaacaa gggggatgtc atccctggtg taaagatgct gtgcaggaag tcagcactca  780
cgggatccag gggacgctcc aaggggaatc cccagggcct gccatccatc cgggaagaga  840
gcaaatgcta cccatgagga cctcctcact cccttttgc tctttcttcc actcagatcc  900
accccactcc accccaccc aaatcccagt gacctttgac taaagggcca aaactgcttc  960
cttttctcac aatgagagtt gtccctccct caatgccaca cacact                 1006

SEQ ID NO: 11           moltype = DNA  length = 1006
FEATURE                 Location/Qualifiers
source                  1..1006
                        mol_type = other DNA
                        organism = synthetic construct
SEQUENCE: 11
ggtgggcgga tcacgaggtc aggagatcaa gaccatcctg gctaacacag taaaacccca  60
tctctactaa atacaaaaaa aaattagccg ggagtgctgg cgggtgcctg tagtcccagc  120
tactcaggag gctgaggcgg gagaatggcg tgaacccagg aggcagagct tgcagtgagc  180
ggagatcgcg ccactgcact ccagcctggg caacagagcg agattccgtc taaaaaaaaa  240
aaaaaagaat gttgtgataa aaggtgatgc tcacctctcc cacacccttt tatagtttag  300
ggattgtatt tccaaggttt ctagactgag agcccttttc atctttgctc attgacactc  360
tgtacccatt aatcctcctt attagctccc cttcaatgga cacatgggta gtcagggtgc  420
aggtctcaga actgtccttc aggttccagg tgatcaacca agtgccttgt ctgtagtgtc  480
aactcattgc tgccccttcc gaattctagt aatccccata atttagctct ccatttcata  540
gtctttcctt gggtgtgtta aaagtgacca tggtacactc agcacggatg aaatgaaaca  600
gtgtttagaa acgtcagtct tctcttttgt aatgccctgt agtctctctg tatgttatat  660
gtcacatttt gtaattaaca gcttgctggt gaaaaggacc ccacgaagtg ttggatataa  720
gccagactgt aagtgaatta cttttttgt caatcattta accatcttta acctaaaaga  780
```

-continued

```
gttttatgtg aaatggctta taattgctta gagaatattt gtagagaggc acatttgcca  840
gtattagatt taaaagtgat gttttcttta tctaaatgat gaattatgat tctttttagt  900
tgttggattt gaaattccag acaagtttgt tgtaggatat gcccttgact ataatgaata  960
cttcagggat ttgaatgtaa gtaattgctt ctttttctca ctcatt                1006

SEQ ID NO: 12          moltype = DNA  length = 1006
FEATURE                Location/Qualifiers
source                 1..1006
                       mol_type = other DNA
                       organism = synthetic construct
SEQUENCE: 12
aaggagctgt gattatccca aggtggggat tgtgaatgtg tttgtattgt tctaaactgg  60
gagaaacagg ctgggtgtgt tggcttatgc ctgtaatctc agcactttgg gaggccaagg  120
tgggaggatc acttgagtcc aggagttcaa ggccaccctg ggcaacaggc aaaaaataga  180
gaccccatct ctatttttta aaaataaaat aaactgggag aaagaagcag ggtcctcccc  240
agagcatctt tatccctagt cacagacctg acacctgtgt tgggcaatgg ctacttctag  300
attgtttacc cctactggga cttgtggtga acatatgcac actttggttt acagttggga  360
cccctgattt tagcaggatg gcccaatgga atcagctaca gcagcttgac acacggtacc  420
tggagcagct ccatcagctc tacagtgaca gcttcccaat ggagctgcgg cagtttctgg  480
ccccttggat tgagagtcaa gaattcgatt ggtaagtcct tcttaagtga ctctccaaat  540
tgttaggttt cagtttgagt caagagacat gaactcttaa tgtcatgcct tgctgttcca  600
ttaaaaaatg tatgggtaca ggtgatgggg aaaatgagat caggagataa aggggcaccc  660
tttggtcttg taaagccttt tttatcttag aagggcatgt gggcaactgt ctttgacaca  720
ttgaaaccgc ctgtatggtg gtggatgtct tgaaggttga tttggacctc atttacttgg  780
gcagatcctc tatatattct gataatccag tgatgtggta gacatatttt ttctctgaat  840
gtgaattctg tcatagctag aactttgggt tgatacttgt aattcccctt tagttaaagg  900
aaggagccac aggggtgtat tagtctgttc tcaatttgct ataaagaaat acctgagact  960
gggtaattta taagaaaaga ggtttaatcg gctcatagtt ctgcag                1006

SEQ ID NO: 13          moltype = DNA  length = 606
FEATURE                Location/Qualifiers
source                 1..606
                       mol_type = other DNA
                       organism = synthetic construct
SEQUENCE: 13
aaaataaaat aaactgggag aaagaagcag ggtcctcccc agagcatctt tatccctagt  60
cacagacctg acacctgtgt tgggcaatgg ctacttctag attgtttacc cctactggga  120
cttgtggtga acatatgcac actttggttt acagttggga cccctgattt tagcaggatg  180
gcccaatgga atcagctaca gcagcttgac acacggtacc tggagcagct ccatcagctc  240
tacagtgaca gcttcccaat ggagctgcgg cagtttctgg ccccttggat tgagagtcaa  300
gaattcgatt ggtaagtcct tcttaagtga ctctccaaat tgttaggttt cagtttgagt  360
caagagacat gaactcttaa tgtcatgcct tgctgttcca ttaaaaaatg tatgggtaca  420
ggtgatgggg aaaatgagat caggagataa aggggcaccc tttggtcttg taaagccttt  480
tttatcttag aagggcatgt gggcaactgt ctttgacaca ttgaaaccgc ctgtatggtg  540
gtggatgtct tgaaggttga tttggacctc atttacttgg gcagatcctc tatatattct  600
gataat                                                            606

SEQ ID NO: 14          moltype = DNA  length = 206
FEATURE                Location/Qualifiers
source                 1..206
                       mol_type = other DNA
                       organism = synthetic construct
SEQUENCE: 14
gcagcttgac acacggtacc tggagcagct ccatcagctc tacagtgaca gcttcccaat  60
ggagctgcgg cagtttctgg ccccttggat tgagagtcaa gaattcgatt ggtaagtcct  120
tcttaagtga ctctccaaat tgttaggttt cagtttgagt caagagacat gaactcttaa  180
tgtcatgcct tgctgttcca ttaaaa                                      206

SEQ ID NO: 15          moltype = DNA  length = 25
FEATURE                Location/Qualifiers
source                 1..25
                       mol_type = other DNA
                       organism = synthetic construct
SEQUENCE: 15
gaggtagttg ggacactcga tgaag                                       25

SEQ ID NO: 16          moltype = DNA  length = 25
FEATURE                Location/Qualifiers
source                 1..25
                       mol_type = other DNA
                       organism = synthetic construct
SEQUENCE: 16
tgctggggaa tgggtctctc tgtgg                                       25

SEQ ID NO: 17          moltype = DNA  length = 25
FEATURE                Location/Qualifiers
source                 1..25
                       mol_type = other DNA
                       organism = synthetic construct
```

-continued

```
SEQUENCE: 17
atcgctagag cccaagaagt caagg                                    25

SEQ ID NO: 18          moltype = DNA  length = 25
FEATURE                Location/Qualifiers
source                 1..25
                       mol_type = other DNA
                       organism = synthetic construct
SEQUENCE: 18
tgactaatgg gaaccatcag tctgt                                    25

SEQ ID NO: 19          moltype = DNA  length = 20
FEATURE                Location/Qualifiers
source                 1..20
                       mol_type = other DNA
                       organism = synthetic construct
SEQUENCE: 19
gcagcagatg ctgctatgct                                          20

SEQ ID NO: 20          moltype = DNA  length = 33
FEATURE                Location/Qualifiers
source                 1..33
                       mol_type = other DNA
                       organism = synthetic construct
SEQUENCE: 20
tcacacactt ctggtagata atggattcta gaa                           33

SEQ ID NO: 21          moltype = AA  length = 15
FEATURE                Location/Qualifiers
source                 1..15
                       mol_type = protein
                       organism = synthetic construct
SEQUENCE: 21
GLNDIFEAQK IEWHE                                               15

SEQ ID NO: 22          moltype = AA  length = 26
FEATURE                Location/Qualifiers
source                 1..26
                       mol_type = protein
                       organism = synthetic construct
SEQUENCE: 22
KRRWKKNFIA VSAANRFKKI SSSGAL                                   26

SEQ ID NO: 23          moltype = AA  length = 13
FEATURE                Location/Qualifiers
source                 1..13
                       mol_type = protein
                       organism = synthetic construct
SEQUENCE: 23
GAPVPYPDPL EPR                                                 13

SEQ ID NO: 24          moltype = AA  length = 8
FEATURE                Location/Qualifiers
source                 1..8
                       mol_type = protein
                       organism = synthetic construct
SEQUENCE: 24
DYKDDDDK                                                       8

SEQ ID NO: 25          moltype = AA  length = 9
FEATURE                Location/Qualifiers
source                 1..9
                       mol_type = protein
                       organism = synthetic construct
SEQUENCE: 25
YPYDVPDYA                                                      9

SEQ ID NO: 26          moltype = AA  length = 6
FEATURE                Location/Qualifiers
source                 1..6
                       mol_type = protein
                       organism = synthetic construct
SEQUENCE: 26
HHHHHH                                                         6

SEQ ID NO: 27          moltype = AA  length = 10
FEATURE                Location/Qualifiers
source                 1..10
                       mol_type = protein
```

```
                         organism = synthetic construct
SEQUENCE: 27
EQKLISEEDL                                                          10

SEQ ID NO: 28            moltype = AA  length = 18
FEATURE                  Location/Qualifiers
source                   1..18
                         mol_type = protein
                         organism = synthetic construct
SEQUENCE: 28
TKENPRSNQE ESYDDNES                                                 18

SEQ ID NO: 29            moltype = AA  length = 15
FEATURE                  Location/Qualifiers
source                   1..15
                         mol_type = protein
                         organism = synthetic construct
SEQUENCE: 29
KETAAAKFER QHMDS                                                    15

SEQ ID NO: 30            moltype = AA  length = 38
FEATURE                  Location/Qualifiers
source                   1..38
                         mol_type = protein
                         organism = synthetic construct
SEQUENCE: 30
MDEKTTGWRG GHVVEGLAGE LEQLRARLEH HPQGQREP                           38

SEQ ID NO: 31            moltype = AA  length = 13
FEATURE                  Location/Qualifiers
source                   1..13
                         mol_type = protein
                         organism = synthetic construct
SEQUENCE: 31
SLAELLNAGL GGS                                                      13

SEQ ID NO: 32            moltype = AA  length = 8
FEATURE                  Location/Qualifiers
source                   1..8
                         mol_type = protein
                         organism = synthetic construct
SEQUENCE: 32
TQDPSRVG                                                            8

SEQ ID NO: 33            moltype = AA  length = 8
FEATURE                  Location/Qualifiers
source                   1..8
                         mol_type = protein
                         organism = synthetic construct
SEQUENCE: 33
WSHPQFEK                                                            8

SEQ ID NO: 34            moltype = AA  length = 6
FEATURE                  Location/Qualifiers
source                   1..6
                         mol_type = protein
                         organism = synthetic construct
SEQUENCE: 34
CCPGCC                                                              6

SEQ ID NO: 35            moltype = AA  length = 14
FEATURE                  Location/Qualifiers
source                   1..14
                         mol_type = protein
                         organism = synthetic construct
SEQUENCE: 35
GKPIPNPLLG LDST                                                     14

SEQ ID NO: 36            moltype = AA  length = 11
FEATURE                  Location/Qualifiers
source                   1..11
                         mol_type = protein
                         organism = synthetic construct
SEQUENCE: 36
YTDIEMNRLG K                                                        11

SEQ ID NO: 37            moltype = AA  length = 8
FEATURE                  Location/Qualifiers
source                   1..8
```

-continued

```
                      mol_type = protein
                      organism = synthetic construct
SEQUENCE: 37
DLYDDDDK                                                   8

SEQ ID NO: 38         moltype = AA  length = 16
FEATURE               Location/Qualifiers
source                1..16
                      mol_type = protein
                      organism = synthetic construct
SEQUENCE: 38
TDKDMTITFT NKKDAE                                          16

SEQ ID NO: 39         moltype = AA  length = 13
FEATURE               Location/Qualifiers
source                1..13
                      mol_type = protein
                      organism = synthetic construct
SEQUENCE: 39
AHIVMVDAYK PTK                                             13

SEQ ID NO: 40         moltype = AA  length = 12
FEATURE               Location/Qualifiers
source                1..12
                      mol_type = protein
                      organism = synthetic construct
SEQUENCE: 40
KLGDIEFIKV NK                                              12
```

UBIQUITIN VARIANT WITH HIGH AFFINITY FOR BINDING 53BP1 REDUCES THE AMOUNT OF AAV NEEDED TO ACHIEVE HIGH RATES OF HDR

CROSS-REFERENCE TO RELATED APPLICATIONS

This application claims benefit of priority under 35 U.S.C. 119 to U.S. Provisional Patent Application Ser. No. 63/399,452, filed Aug. 19, 2022, entitled "A UBIQUITIN VARIANT WITH HIGH AFFINITY FOR BINDING 53BP1 REDUCES THE AMOUNT OF AAV NEEDED TO ACHIEVE HIGH RATES OF HDR," the contents of which is herein incorporated by reference in its entirety.

SEQUENCE LISTING

The instant application contains a Sequence Listing which has been submitted in XML format via Patent Center and is hereby incorporated by reference in its entirety. Said XML copy, created on Aug. 15, 2023, which is 39,904 bytes in size, is named IDT01-023-PCT ST26.xml.

FIELD OF THE INVENTION

This invention pertains to the ability of a ubiquitin variant to bind to 53BP1 and bias the repair of a double-strand break (DSB) towards homology directed repair (HDR).

BACKGROUND OF THE INVENTION

Double-strand breaks (DSBs) are predominantly repaired through two mechanisms, non-homologous end joining (NHEJ), in which broken ends are rejoined, often imprecisely, or homology directed repair (HDR), which typically involves a sister chromatid or homologous chromosome being used as a repair template. HDR is facilitated by the presence of a sister chromatid and there are cellular mechanisms in place biasing repair towards NHEJ during the G1 phase of the cell cycle [1]. A key determinant of repair pathway choice is 53BP1. 53BP1 was first described as a binding partner of the tumor suppressor gene p53 and was later shown to be a key protein in NHEJ [2]. 53BP1 rapidly accumulates at sites of double strand breaks. In G1, 53BP1 recruits RIF1 and inhibits end resection [3, 4]. End resection is a critical step in repair pathway choice, as it is necessary for HDR and inhibits NHEJ [1]. By inhibiting end resection, 53BP1 biases repair towards NEHJ and consequently loss of 53BP1 results in increased HDR [5]. Targeted nucleases can be introduced into cells in conjunction with a DNA repair template with homology to a targeted cut site to facilitate precise genome editing via HDR [6]. A strong inhibitor of 53BP1 is therefore useful for precise genome editing.

The recruitment of 53BP1 to DSB sites is dependent upon both H4K20 methylation and H2AK15 ubiquitination. 53BP1 has tandem Tudor domains that have been shown to specifically bind mono and demethylated H4K20 and H4K20 methylation was shown to be important for 53BP1 recruitment to double strand breaks [7, 8]. Introducing D1521R, a mutation that disrupts the activity of the Tudor domain, impairs the ability of 53BP1 to form ionizing radiation-induced foci [9]. The minimal focus-forming region of 53BP1 consists of the Tudor domain flanked by an N-terminal oligomerization region and a C-terminal extension. Notably, 53BP1 accumulation at DSBs requires the E3 ubiquitin ligase RNF168, that mediates H2AK13 and H2AK15 ubiquitination [10]. The C-terminal extension was shown to contain a ubiquitination-dependent recruitment motif (UDR) that binds specifically to H2AK15ub and is required for 53BP1 recruitment to DSB sites [9].

Due to the affinity of 53BP1 for ubiquitinated H2A, a screen of ubiquitin variants for interaction with 53BP1 was conducted recently by Canny et al. in which they discovered and modified a ubiquitin variant with selective binding to 53BP1 that they named i53 (inhibitor of 53BP1) [11]. The top five hits from the ubiquitin variant screen were A10, A11, C08, G08, and H04, with G08 having the highest affinity. In contrast to what might be expected, the interaction of 53BP1 with G08 did not require the UDR and the interaction was shown to be between G08 and the 53BP1 Tudor domain. To generate i53, G08 was modified by introducing an I44A mutation that disrupts a solvent exposed hydrophobic patch on ubiquitin that most ubiquitin binding proteins interact with [9, 12]. Notably, this mutation in the context of $H2AK_C15ub(I44A)$ interferes with 53BP1 interaction with ubiquitinated H2A, yet does not interfere with the ability of i53 to enhance HDR, consistent with i53 enhancing HDR through interaction with the 53BP1 Tudor domain and not the UDR domain [9, 11]. Additionally, i53 was modified relative to G08 through the removal of the C-terminal di-glycine motif. Introduction of i53, but not a 53BP1 binding deficient i53 variant DM (i53 P69L+L70V), into cells inhibited the formation ionizing radiation induced 53BP1 foci. Introduction of i53 via plasmid delivery, adeno-associated virus mediated gene delivery, or delivery of mRNA were all shown to improve the rates of HDR. Rates of HDR were improved with the introduction of i53 using both double-stranded DNA donors and using single-stranded DNA donors, which have been shown to use different HDR mechanisms [11, 13, 14].

A previous filing (U.S. Provisional Patent Application Ser. No. 63/321,384, filed Mar. 18, 2022 to Vakulskas et al., entitled "UBIQUITIN VARIANTS WITH IMPROVED AFFINITY FOR 53BP1" described the invention of a ubiquitin variant that contained 9 amino acid substitutions relative to i53 that had dramatically improved affinity for binding 53BP1 (50-100 fold) that we called CM1. We demonstrated that this ubiquitin variant was able to enhance HDR to a greater degree and at lower doses than i53 in when short ssDNA Alt-R donor oligos and long dsDNA Alt-R HDR donor blocks were used as the donor template.

The present disclosure pertains to improved methods for improving HDR in recipient cells by introducing CM1 into the cells when using adeno-associated virus (AAV) for template delivery.

BRIEF SUMMARY OF THE INVENTION

In a first aspect, a nucleic acid sequence encoding a tag-free ubiquitin polypeptide variant CM1 is provided.

In a second aspect, the protein sequence of a tag-free CM1 polypeptide is provided.

In a third aspect, a method for improving homology directed repair (HDR) in a recipient cell is provided. The method includes the step of introducing a nucleic acid donor template and an isolated tag-free CM1 polypeptide into the recipient cell.

BRIEF DESCRIPTION OF THE DRAWINGS

In FIG. 1A-C, the ubiquitin variant CM1tf boosts HDR when delivered with Cas9 RNP when an AAV vector is used to deliver the donor template. The heatmaps show the percent HDR measured by EcoR1 cleavage assay with and without the use of CM1tf. Cas9 RNP (2 μM) was delivered with and without CM1tf into cells by Lonza nucleofection using 4 μM Alt-R Cas9 Electroporation Enhancer. AAV donor containing an EcoR1 cut site insert with 500 bp homology arms was added at a range of multiplicity of infection (MOIs) to cells for 24 hours following RNP delivery. Editing is displayed as average percent HDR±standard deviation for three biological replicates.

In FIG. 2A-B, the ubiquitin variant CM1tf boosts HDR provides an additional boost when used with Alt-R HDR enhancer V2. The heatmaps shows the percent HDR measured by EcoR1 cleavage assay with use of CM1tf, Alt-R HDR enhancer V2 (V2), or both. Cas9 RNP was co-delivered with and without CM1tf into cells by Lonza nucleofection with 2 μM Cas9 RNP, 4 μM Alt-R Cas9 Electroporation Enhancer, and 0 or 25 uM CM1tf. AAV donor containing an EcoR1 cut site insert with 500 bp homology arms was added at a range of MOIs to cells for 24 hours following RNP delivery. V2 enhancer was added to media at a 1 uM final concentration for 24 hours following nucleofection. Editing is displayed as average percent HDR±standard deviation for three biological replicates.

DETAILED DESCRIPTION OF THE INVENTION

The current invention identifies how well CM1 is able to improve HDR when using adeno-associated virus (AAV) for template delivery into cells. Consideration of what donor is used is especially important when working with primary cells, as different donors including plasmid DNA, linear dsDNA, ssODN have differences the amount of cytotoxicity they cause which can drastically affect overall cell yields [15-17]. Use of AAV is often a preferred method for delivering DNA template into cells due to the ability to introduce large sequences while avoiding the high toxicity associated with naked double stranded DNA [18-21]. However, there is still a tradeoff, a higher multiplicity of infection (MOI) can give higher editing levels at the cost of increased toxicity resulting in lower cell yields. AAV production is also time consuming and expensive. Therefore, any product that can reduce the amount of AAV needed to achieve high levels of editing could increase cell yields and improved rates of HDR while reducing manufacturing costs.

Applications

In a first aspect, an isolated nucleic acid sequence encoding a tag-free CM1 polypeptide is provided. In a first respect, the isolated nucleic acid sequence encodes CM1tf polypeptide.

In a second aspect, an isolated protein sequence of a tag-free CM1 polypeptide is provided. In a first respect, the tag-free CM1 polypeptide includes CM1tf polypeptide.

In a third aspect, a method for improving homology directed repair (HDR) in a recipient cell is provided. The method includes the step of introducing a nucleic acid donor template and an isolated tag-free CM1 polypeptide into the recipient cell. In a first respect, the nucleic acid donor template includes an Adeno virus-associated vector. In a second respect, the isolated tag-free CM1 polypeptide comprises CM1tf polypeptide.

EXAMPLES

Example 1

Figure 1A:
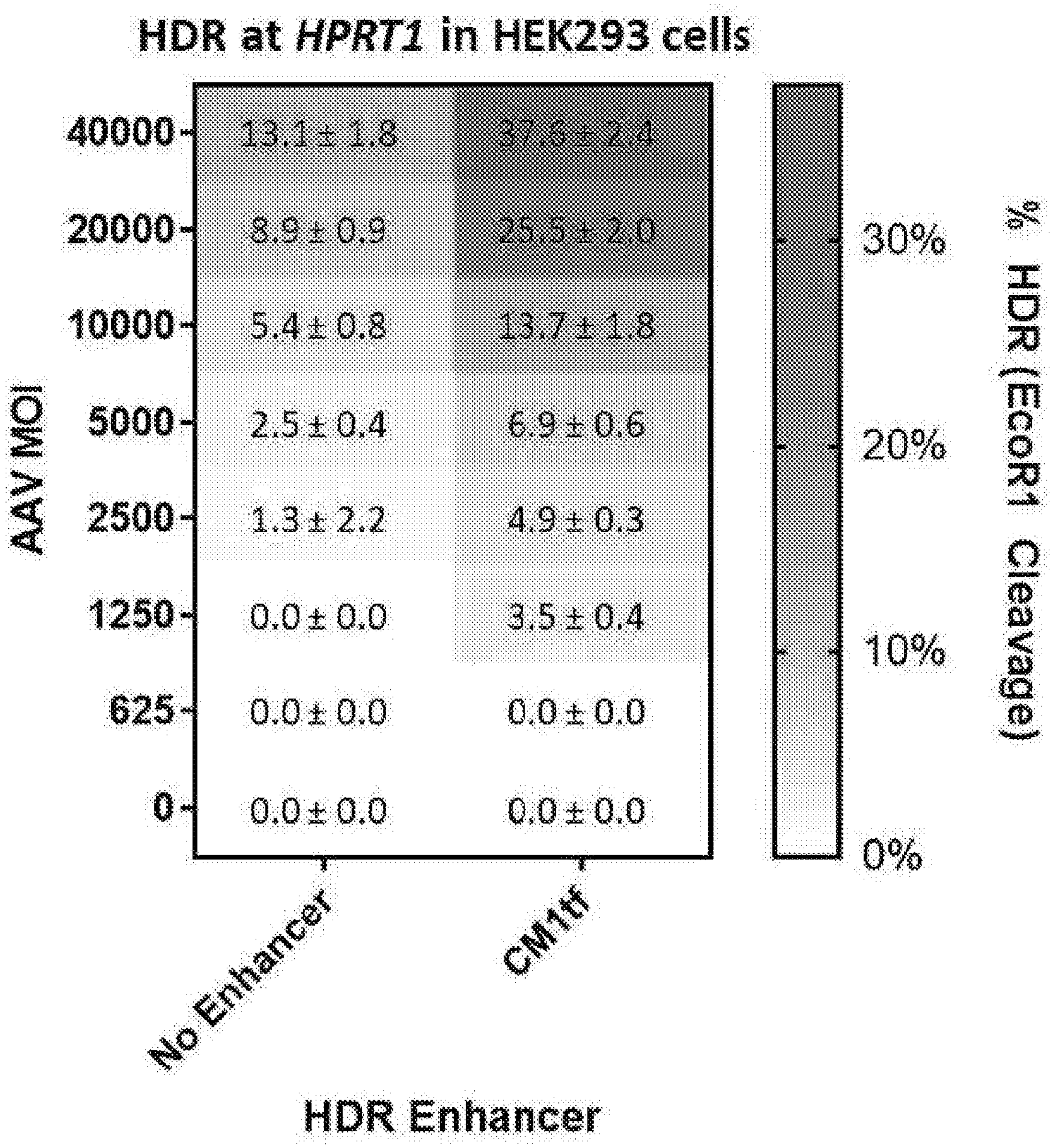
FIG. 1A depicts an exemplary heatmap showing the percent HDR at HPRT1 in HEK293 cells with and without 25 uM CM1tf.
Figure 1B:
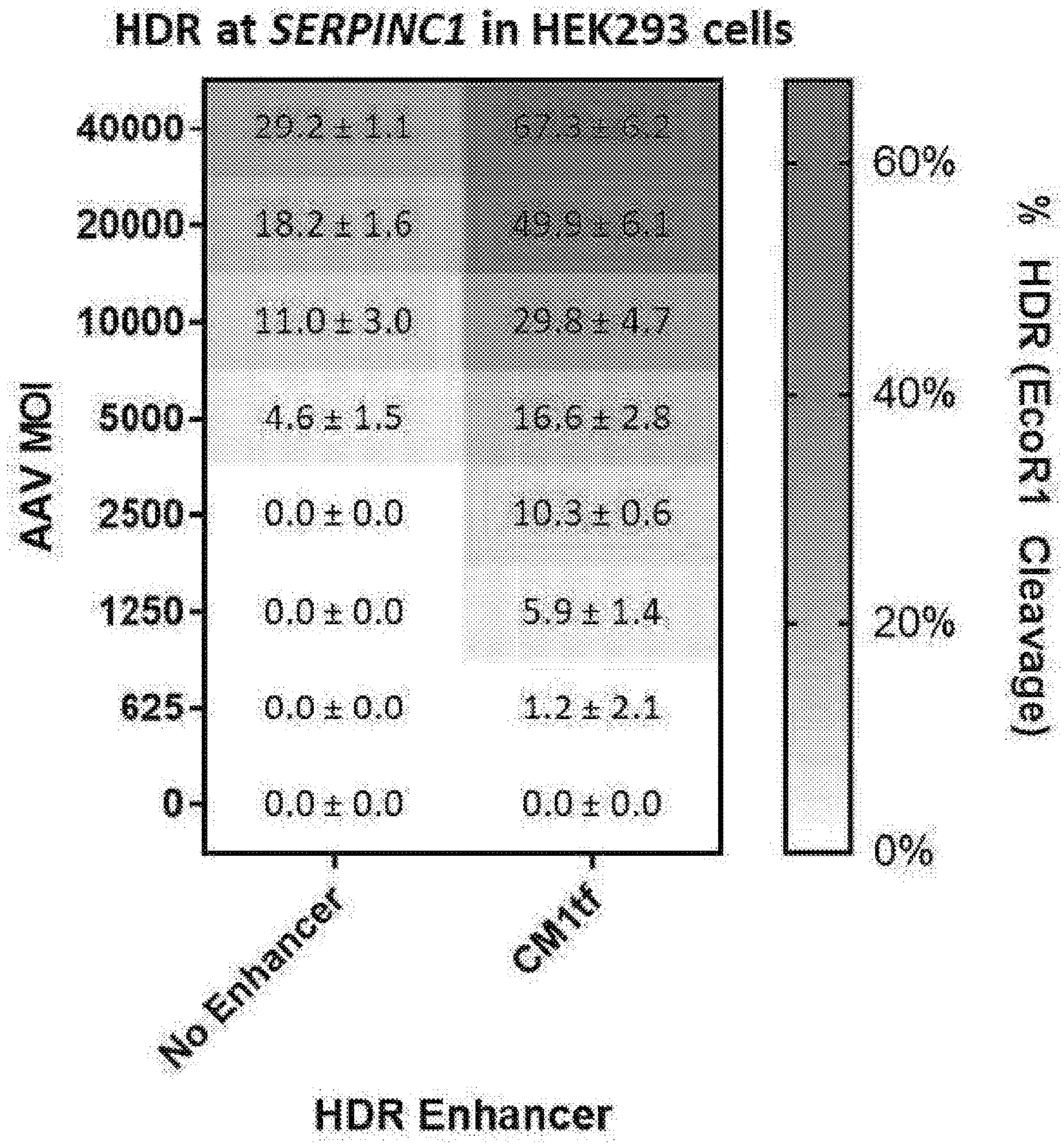
FIG. 1B depicts an exemplary heatmap showing the percent HDR at SERPINC1 in HEK293 cells with and without 25 uM CM1tf.
Figure 1C:
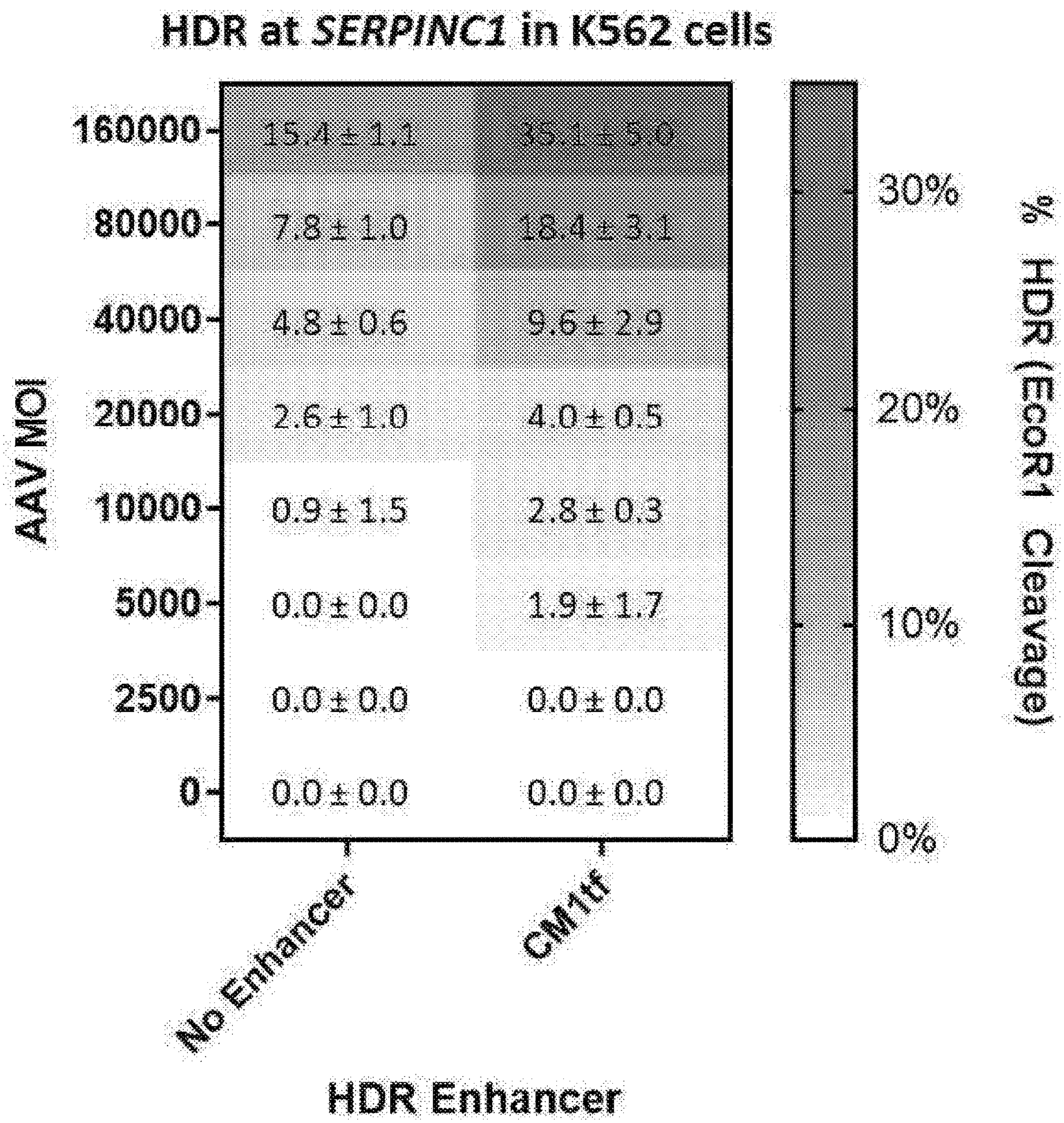
FIG. 1C depicts an exemplary heatmap showing the percent HDR at SERPINC1 in K562 cells with and without 50 uM CM1tf.

Tag-Free CM1 (CM1tf) Boosts HDR When AAV is Used for Repair Template Delivery We developed at tag-free version of CM1 (CM1tf) and tested its ability to enhance HDR in cell lines using AAV donor (see Table 1). AAV-DJ, a synthetic AAV serotype most closely related to AAV-2 that is a chimera of type 2/type 8/and type 9, was chosen for testing due to its high transduction efficiency in vitro for a broad range of cell types [22]. The dose of CM1tf was held constant while a range of MOIs was used for the AAV donor. The AAV donor was constructed such that a 6 base pair insert consisting of an EcoR1 cut site (GAATTC) was flanked by 500 base pairs of homology arm matching the genomic sequence on either side of the target cut site. Briefly, Cas9 V3 protein (IDT) and Alt-R sgRNA (IDT) were mixed at a 1:1.2 ratio, incubated for 10 min, then Alt-R Cas9 electroporation enhancer (EE) (IDT), 1×PBS (Gibco), and CM1tf, diluted in 1×PBS, were added. HEK293 or K562 cells were washed and resuspended in SF buffer for Lonza Nucleofection and added to the RNP+DNA mix such that the final concentration of Cas9 RNP was 2 μM, EE was 4 μM, and CM1tf was 25 μM (HEK293 cells) or 50 μM (K562 cells). Cells plus RNP+DNA were electroporated using program DS-150 (HEK293 cells) or FF-120 (K562 cells) using the Lonza nucleofector system. Cells were then plated in 96 well plates at 20,000 cells/well and AAV was added to the wells at a range of MOI from 0 (no virus) to 160,000, with MOI being calculated as viral genomes (vg) per cell with vg calculated using qPCR. Cells were recovered and plated with serum free media, AAV was added, then serum containing media was added after four hours. Genomic DNA was isolated 48 hours after RNP delivery using QuickExtract (Lucigen). The results are shown in FIG. 1. Use of CM1tf dramatically boosted HDR rates such that approximately four-fold less AAV was needed to achieve the same level of editing as without the CM1tf HDR enhancer in HEK293 cells.

Example 2

Figure 2A:
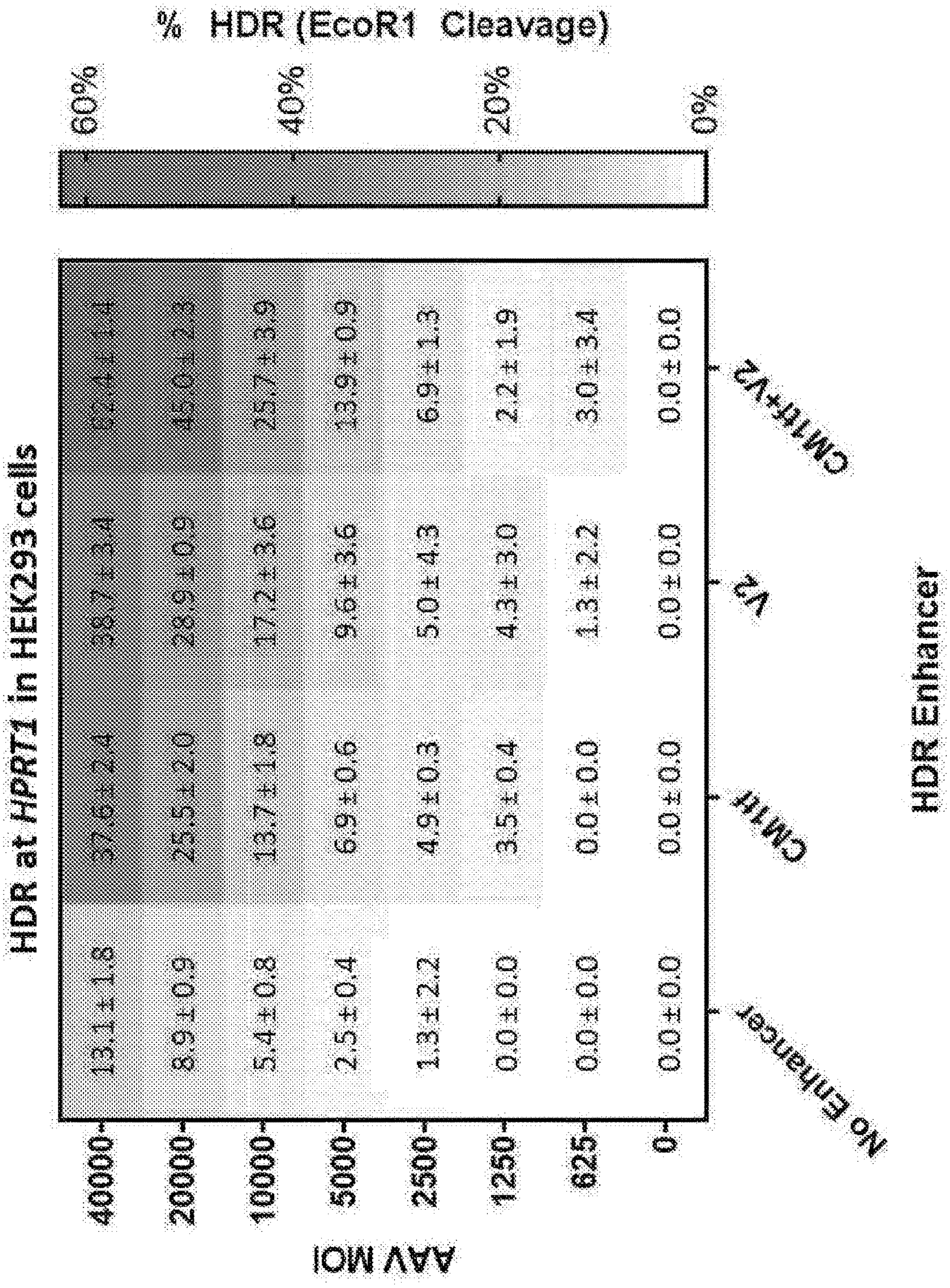
FIG. 2A depicts an exemplary heatmap showing the percent HDR at HPRT1 in HEK293 cells with no enhancer, CM1tf, Alt-R HDR enhancer V2 ("V2"), or CM1tf+V2.
Figure 2B:
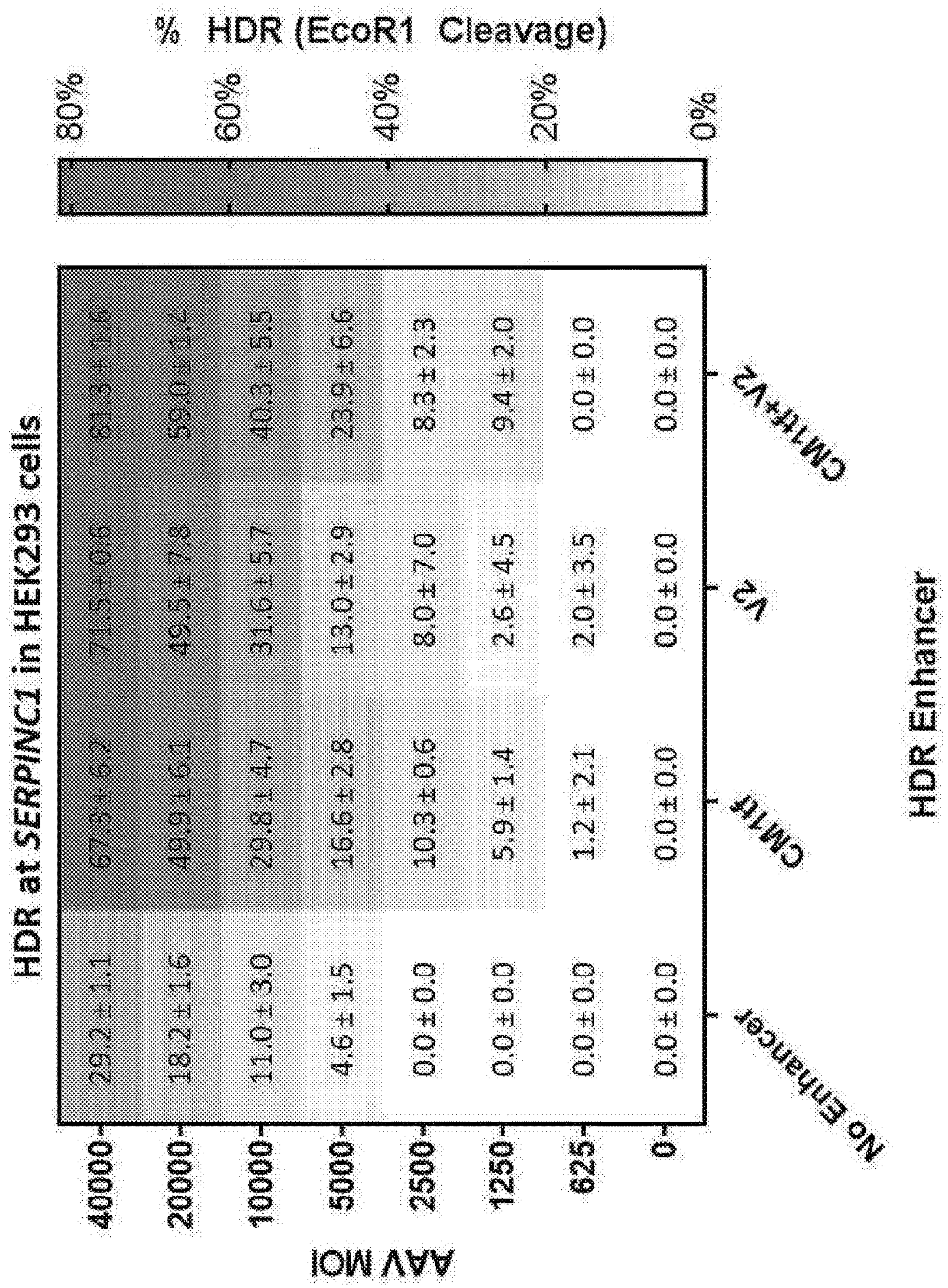
FIG. 2B depicts an exemplary heatmap showing the percent HDR at SERPINC1 in HEK293 cells with no enhancer, CM1tf, V2, or CM1tf+V2.

CM1tf Can be Used in Combination with Alt-R HDR Enhancer V2 to Further Boost HDR When Using AAV Donor In order to optimize HDR, it is often desirable to use a combination of HDR enhancers that work by different mechanisms to further boost HDR rates beyond what can be achieved by any single enhancer alone [23]. Because CM1tf works by facilitating end resection, and thus promoting HDR, it is possible that it could be combined with IDT Alt-R HDR enhancer V2, an inhibitor of NHEJ, to further boost HDR. To test this, Cas9 RNP with or without added CM1tf was delivered into HEK293 cells as described in example one, and cells were then plated in media with or without 1 μM V2 enhancer, with AAV then added to each well in a range of MOIs as described previously. The results of this testing are shown in FIG. 2. Use of CM1tf or V2 enhancer resulted in approximately equivalent improvement in HDR rates, however use of them together provided an additional improvement in HDR beyond what either enhancer was able to achieve individually.

Example 3

Figure 3:
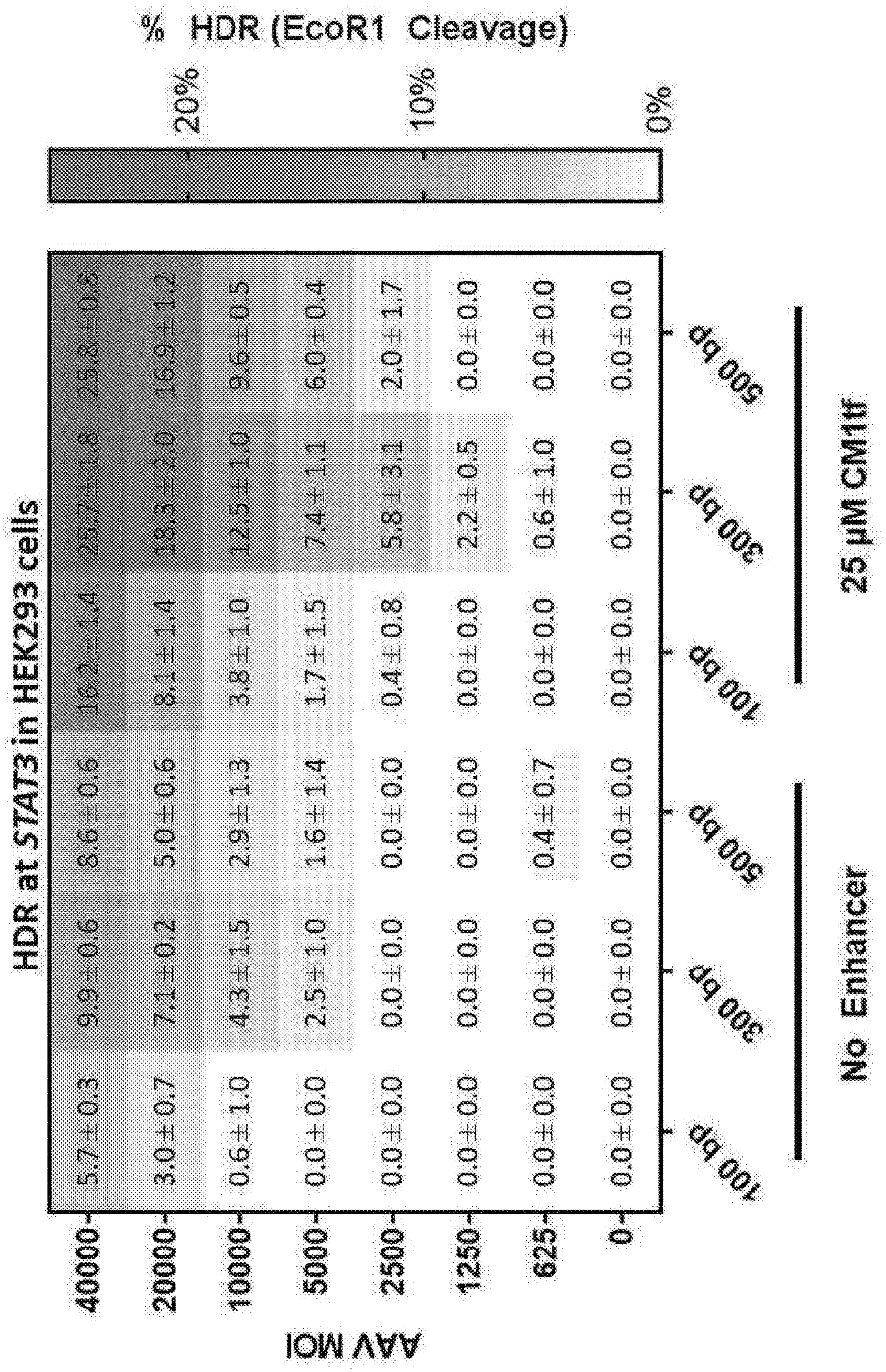
FIG. 3 summarizes exemplary heatmaps showing IDT ubiquitin variant CM1tf boosts HDR when used with AAV donors possessing different homology arm lengths. The heatmaps show the percent HDR at STAT3 measured by EcoR1 cleavage assay with or without CM1tf. Cas9 RNP was co-delivered with and without CM1tf into cells by Lonza nucleofection with 2 μM Cas9 RNP, 4 μM Alt-R Cas9 Electroporation Enhancer, and 0 or 25 uM CM1tf. AAV donor containing 500 base pair (bp), 300 bp, or 100 bp homology arms was added at a range of MOIs to cells for 24 hours following RNP delivery. Editing is displayed as average percent HDR±standard deviation for three replicates (single nucleofection, separate AAV delivery and downstream processing).

CM1tf Provides a Boost to HDR When Used With AAV Packaged Donor DNA Templates With Various Homology Arm Lengths In order to test the compatibility of CM1tf with AAV donors with differing homology arm lengths and to identify the optimal HA length for short inserts we tested the effect of CM in combination with AAV donors containing 100, 300, or 500 bp homology arms. RNP and CM1tf were delivered into HEk293 cells as described in Example 1. The results are shown in FIG. 3. The 300 bp homology arm donor provided the highest rate of HDR without enhancers and this trend was maintained with the addition of CM1tf. Use of CM1tf resulted in a similar level of boost to HDR rates regardless of homology arm length.

Example 4

CM1tf Outperforms i53 in its Ability to Boost HDR With AAV Donor

Figure 4:
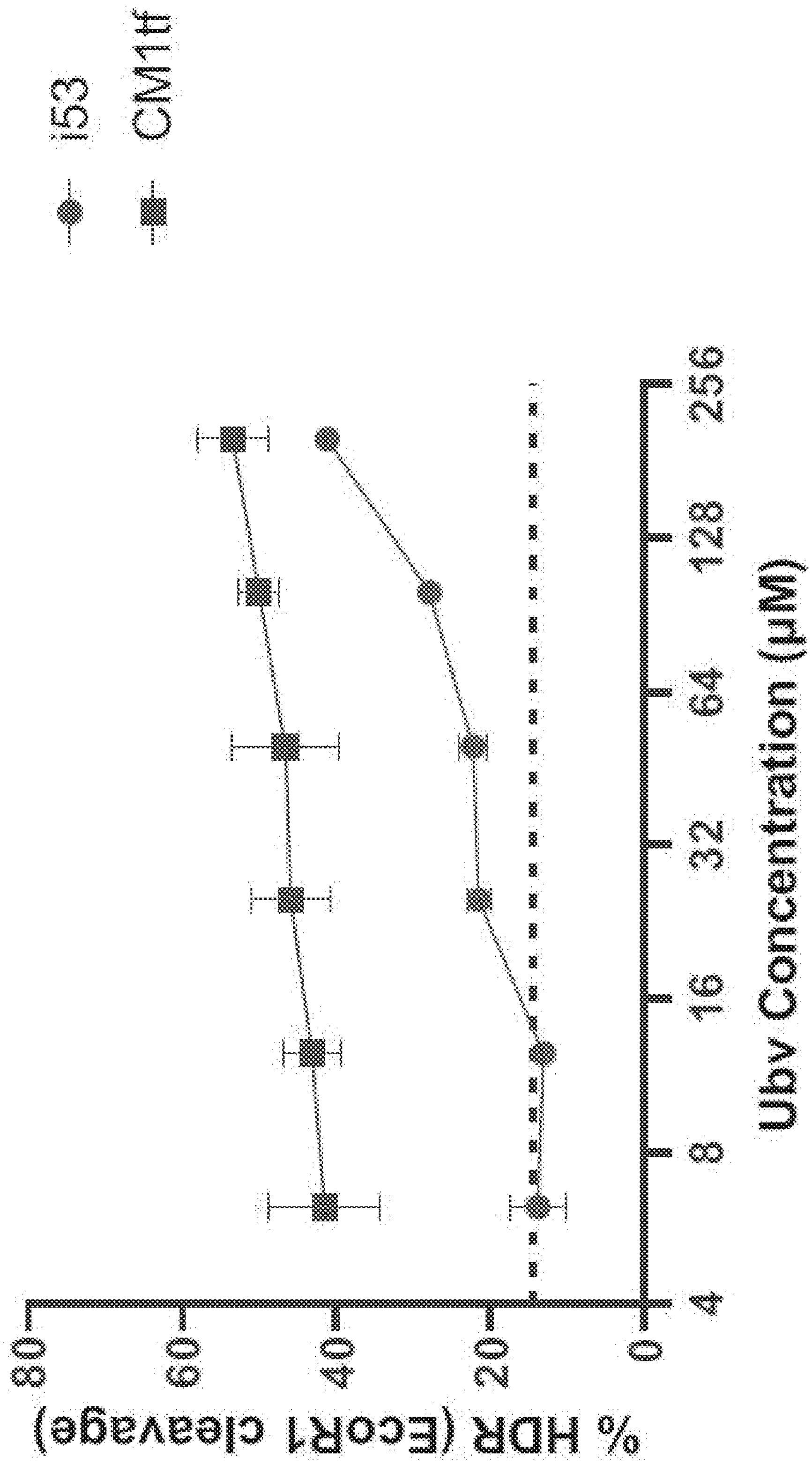
FIG. 4 illustrates that CM1tf outperforms i53 in its ability to boost HDR with AAV donor. The graph shows the percent HDR measured by EcoR1 cleavage assay with use of CM1tf. Cas9 RNP was co-delivered with and without CM1tf into cells by Lonza nucleofection with 2 μM Cas9 RNP, 4 μM Alt-R Cas9 Electroporation Enhancer, and range of CM1tf concentrations from 200 μM to 6.25 μM. AAV donor containing an EcoR1 cut site insert with 500 bp homology arms was added at an MOI of 20,000 to cells for 24 hours following RNP delivery. Editing is displayed as average percent HDR with bars indicating standard deviation for three biological replicates.

Achieving the best possible rate of HDR using AAV donor may require a different optimal dose CM1tf compared to when using ssDNA donor. Furthermore, the nature of the donor may affect the benefit of using CM1tf compared to i53. To test this, Cas9 RNP was co-delivered with either CM1tf and i53 in a range of doses into HEK293 cells as described in example one with AAV added to cells for 24 hours afterward at a set MOI of 20,000. The results are shown in FIG. 4. Previous testing of CM with ssDNA donor showed CM had approximately the same benefit to HDR over a dosage range from 6.25 to 50 μM, and that the optimal concentration for i53 was around 100-150 μM, with a decrease in benefit at 200 μM. Here we showed that with AAV donor, while CM1tf continued to outperform i53, higher doses of CM1tf up to 200 μM did provide slightly larger benefit to HDR with increasing dose. This was even more notable for i53, which had a large performance increase going from 100 μM to 200 μM, despite this not being a trend observed with ssDNA donor. These results indicate that the nature of the donor used is an important consideration for dosing CM1tf. However, the benefit to HDR of CM1tf is much less affected by dose compared to i53, and overall higher editing levels were achieved with CM1tf compared to i53.

Example 5

Sequences

TABLE 1

Amino acid and DNA sequences

| Name (SEQ ID NO)[a] | Amino acid changes relative to i53 | Protein Sequence | DNA sequence |
|---|---|---|---|
| i53 (SEQ ID NO: 1; SEQ ID NO: 4) | None | MHHHHHHGG SGMLIFVKTL TGKTITLEVEP SDTIENVKAKI QDKEGIPPDQ QRLAFAGKSL EDGRTLSDYN ILKDSKLHPLL RLR | ATGCACCATCACCACCACCACGGTG GATCTGGCATGTTGATTTTCGTAAAG ACGTTGACTGGAAAGACTATCACTTT GGAAGTGGAGCCTTCCGATACTATCG AGAATGTTAAGGCCAAAATCCAAGA TAAGGAAGGGATTCCTCCAGATCAA CAACGCCTTGCTTTTGCCGGGAAGAG CCTGGAGGACGGTCGCACACTGTCTG ACTATAACATTCTTAAAGATTCTAAA TTGCATCCACTGCTGCGCTTGCGT |
| CM1 (SEQ ID NO: 2; SEQ ID NO: 5) | K6R, T7M, T12M, T14E, K33H, A46Q, | MHHHHHHGG SGMLIFVRML TGKMIELEVE PSDTIENVKA KIQDHEGIPPD QQRLAFQGKS | ATGCACCACCACCACCACCACGGTG GATCTGGCATGTTGATTTTCGTACGC ATGTTGACTGGAAAGATGATCGAGTT GGAAGTGGAGCCTTCCGATACTATCG AGAATGTTAAGGCCAAAATCCAAGA TCATGAAGGGATTCCTCCAGATCAAC |

TABLE 1-continued

| Amino acid and DNA sequences | | | |
|---|---|---|---|
| Name<br>(SEQ ID NO)[a] | Amino acid changes relative to i53 | Protein Sequence | DNA sequence |
| | S65P,<br>L67K,<br>H68M | LEDGRTLSDY<br>NILKDPKKMP<br>LLRLR | AACGCCTTGCTTTTCAAGGGAAGAGC<br>CTGGAGGACGGTCGCACACTGTCTG<br>ACTATAACATTCTTAAAGATCCTAAA<br>AAGATGCCACTGCTGCGCTTGCGT |
| CM1tf<br>(SEQ ID NO: 3;<br>SEQ ID NO: 6) | K6R,<br>T7M,<br>T12M,<br>T14E,<br>K33H,<br>A46Q,<br>S65P,<br>L67K,<br>H68M | MLIFVRMLTG<br>KMIELEVEPS<br>DTIENVKAKI<br>QDHEGIPPDQ<br>QRLAFQGKSL<br>EDGRTLSDYN<br>ILKDPKKMPL<br>LRLR | ATGTTGATTTTCGTACGCATGTTGAC<br>TGGAAAGATGATCGAGTTGGAAGTG<br>GAGCCTTCCGATACTATCGAGAATGT<br>TAAGGCCAAAATCCAAGATCATGAA<br>GGGATTCCTCCAGATCAACAACGCCT<br>TGCTTTTCAAGGGAAGAGCCTGGAG<br>GACGGTCGCACACTGTCTGACTATAA<br>CATTCTTAAAGATCCTAAAAAGATGC<br>CACTGCTGCGCTTGCGT |

[a]The first listed SEQ ID NO corresponds to the amino acid sequence; the second listed SEQ ID NO corresponds to the nucleotide sequence.

TABLE 2

| Guides | | |
|---|---|---|
| Gene | protospacer | Coordinates (hg38) |
| SERPINC1<br>(SEQ ID NO: 7) | ACCTCTGGAAAAAGGTAAGA | chr1:173, 917, 213-173, 917, 232 |
| HPRT1<br>(SEQ ID NO: 8) | AATTATGGGGATTACTAGGA | chrX:134, 498, 212-134, 498, 231 |
| STAT3<br>(SEQ ID NO: 9) | CTTGGATTGAGAGTCAAGAT | chr17:42, 348, 391-42, 348, 410 |

TABLE 3

| AAV donors | |
|---|---|
| AAV Donor | Donor sequence (homology arms plus insert) |
| SERPINC1-500 bp HA<br>(SEQ ID NO: 10) | CTTGTCCCTCTTTGCCTTCTCTAATTAGATATTTCTCTCTCT<br>CTCTCCCTCTCTCCATAAAGAAAACTATGAGAGAGGGTGG<br>GTATGAACCAAGTTTGTTTCCTTGGTTAGTTTCCTAACCAA<br>GTTTGAGGGTATGAACATACTCTCCTTTTCCTTTTCTATAAA<br>GCTGAGGAGAAGAGTGAGGGAGTGTGGGCAAGAGAGGTGG<br>CTCAGGCTTTCCCTGGGCCTGATTGAACTTTAAAACTTCTCTA<br>CTAATTAAACAACACTGGGCTCTACACTTTGCTTAACCCTGGG<br>AACTGGTCATCAGCCTTTGACCTCAGTTCCCCCTCCTGACCAG<br>CTCTCTGCCCCACCCTGTCCTCTGGAACCTCTGCGAGATTTAG<br>AGGAAAGAACCAGTTTTCAGGCGGATTGCCTCAGATCACACT<br>ATCTCCACTTGCCCAGCCCTGTGGAAGATTAGCGGCCATGTA<br>TTCCAATGTGATAGGAACTGTAACCTCTGGAAAAAGGTAGAA<br>TTCAGAGGGGTGAGCTTTCCCCTTGCCTGCCCCTACTGGGTTT<br>TGTGACCTCCAAAGGACTCACAGGAATGACCTCCAACACCTTT<br>GAGAAGACCAGGCCCTCTCCCTGGTAGTTACAGTCAAAGACCT<br>GTTTGGAAGACGTCATTTCAAGTGCTCTCCCTCCCACCCCACCT<br>CTTGGGGTAAGGCCTTTCCTAAGCTACCCCTTGGGTCCCTAGCC<br>TAAGAAACAAGGGGGATGTCATCCCTGGTGTAAAGATGCTGTG<br>CAGGAAGTCAGCACTCACGGGATCCAGGGGACGCTCCAAGGGG<br>AATCCCCAGGGCCTGCCATCCATCCGGGAAGAGAGCAAATGCTA<br>CCCATGAGGACCTCCTCACTCCCTTTTTGCTCTTTCTTCCACTCAG<br>ATCCACCCCACTCCACCCCCACCCAAATCCCAGTGACCTTTGACT<br>AAAGGGCCAAAACTGCTTCCTTTTCTCACAATGAGAGTTGTCCCT<br>CCCTCAATGCCACACACACT |
| HPRT1-500 bp HA<br>(SEQ ID NO: 11) | GGTGGGCGGATCACGAGGTCAGGAGATCAAGACCATCCT<br>GGCTAACACAGTAAAACCCCATCTCTACTAAATACAAAA<br>AAAAATTAGCCGGGAGTGCTGGCGGGTGCCTGTAGTCCC<br>AGCTACTCAGGAGGCTGAGGCGGGAGAATGGCGTGAACC<br>CAGGAGGCAGAGCTTGCAGTGAGCGGAGATCGCGCCACT |

TABLE 3-continued

| AAV donors | |
|---|---|
| AAV Donor | Donor sequence (homology arms plus insert) |
| | GCACTCCAGCCTGGGCAACAGAGCGAGATTCCGTCTAAAA<br>AAAAAAAAAAAGAATGTTGTGATAAAAGGTGATGCTCACC<br>TCTCCCACACCCTTTTATAGTTTAGGGATTGTATTTCCAAGG<br>TTTCTAGACTGAGAGCCCTTTTCATCTTTGCTCATTGACACT<br>CTGTACCCATTAATCCTCCTTATTAGCTCCCCTTCAATGGAC<br>ACATGGGTAGTCAGGGTGCAGGTCTCAGAACTGTCCTTCAG<br>GTTCCAGGTGATCAACCAAGTGCCTTGTCTGTAGTGTCAACT<br>CATTGCTGCCCCTTCCGAATTCTAGTAATCCCCATAATTTAG<br>CTCTCCATTTCATAGTCTTTCCTTGGGTGTGTTAAAAGTGAC<br>CATGGTACACTCAGCACGGATGAAATGAAACAGTGTTTAGA<br>AACGTCAGTCTTCTCTTTTGTAATGCCCTGTAGTCTCTCTGTA<br>TGTTATATGTCACATTTTGTAATTAACAGCTTGCTGGTGAAAA<br>GGACCCCACGAAGTGTTGGATATAAGCCAGACTGTAAGTGAA<br>TTACTTTTTTTGTCAATCATTTAACCATCTTTAACCTAAAAGAG<br>TTTTATGTGAAATGGCTTATAATTGCTTAGAGAATATTTGTAGA<br>GAGGCACATTTGCCAGTATTAGATTTAAAAGTGATGTTTTCTTT<br>ATCTAAATGATGAATTATGATTCTTTTTAGTTGTTGGATTTGAA<br>ATTCCAGACAAGTTTGTTGTAGGATATGCCCTTGACTATAATGA<br>ATACTTCAGGGATTTGAATGTAAGTAATTGCTTCTTTTTCTCACT<br>CATT |
| STAT3-500 bp HA<br>(SEQ ID NO: 12) | AAGGAGCTGTGATTATCCCAAGGTGGGGATTGTGAATGTG<br>TTTGTATTGTTCTAAACTGGGAGAAACAGGCTGGGTGTGTT<br>GGCTTATGCCTGTAATCTCAGCACTTTGGGAGGCCAAGGTG<br>GGAGGATCACTTGAGTCCAGGAGTTCAAGGCCACCCTGGGC<br>AACAGGCAAAAAATAGAGACCCCATCTCTATTTTTTAAAAAT<br>AAAATAAACTGGGAGAAAGAAGCAGGGTCCTCCCCAGAGCA<br>TCTTTATCCCTAGTCACAGACCTGACACCTGTGTTGGGCAATG<br>GCTACTTCTAGATTGTTTACCCCTACTGGGACTTGTGGTGAAC<br>ATATGCACACTTTGGTTTACAGTTGGGACCCCTGATTTTAGCA<br>GGATGGCCCAATGGAATCAGCTACAGCAGCTTGACACACGGT<br>ACCTGGAGCAGCTCCATCAGCTCTACAGTGACAGCTTCCCAAT<br>GGAGCTGCGGCAGTTTCTGGCCCCTTGGATTGAGAGTCAAGAA<br>TTCGATTGGTAAGTCCTTCTTAAGTGACTCTCCAAATTGTTAGG<br>TTTCAGTTTGAGTCAAGAGACATGAACTCTTAATGTCATGCCTT<br>GCTGTTCCATTAAAAAATGTATGGGTACAGGTGATGGGGAAAA<br>TGAGATCAGGAGATAAAGGGGCACCCTTTGGTCTTGTAAAGCC<br>TTTTTTATCTTAGAAGGGCATGTGGGCAACTGTCTTTGACACAT<br>TGAAACCGCCTGTATGGTGGTGGATGTCTTGAAGGTTGATTTGG<br>ACCTCATTTACTTGGGCAGATCCTCTATATATTCTGATAATCCAG<br>TGATGTGGTAGACATATTTTTTCTCTGAATGTGAATTCTGTCATA<br>GCTAGAACTTTGGGTTGATACTTGTAATTCCCCTTTAGTTAAAGG<br>AAGGAGCCACAGGGGTGTATTAGTCTGTTCTCAATTTGCTATAAA<br>GAAATACCTGAGACTGGGTAATTTATAAGAAAAGAGGTTTAATCG<br>GCTCATAGTTCTGCAG |
| STAT3-300 bp HA<br>(SEQ ID NO: 13) | AAAATAAAATAAACTGGGAGAAAGAAGCAGGGTCCTCCCC<br>AGAGCATCTTTATCCCTAGTCACAGACCTGACACCTGTGTT<br>GGGCAATGGCTACTTCTAGATTGTTTACCCCTACTGGGACTT<br>GTGGTGAACATATGCACACTTTGGTTTACAGTTGGGACCCCT<br>GATTTTAGCAGGATGGCCCAATGGAATCAGCTACAGCAGCTT<br>GACACACGGTACCTGGAGCAGCTCCATCAGCTCTACAGTGAC<br>AGCTTCCCAATGGAGCTGCGGCAGTTTCTGGCCCCTTGGATTG<br>AGAGTCAAGAATTCGATTGGTAAGTCCTTCTTAAGTGACTCTC<br>CAAATTGTTAGGTTTCAGTTTGAGTCAAGAGACATGAACTCTT<br>AATGTCATGCCTTGCTGTTCCATTAAAAAATGTATGGGTACAG<br>GTGATGGGGAAAATGAGATCAGGAGATAAAGGGGCACCCTTT<br>GGTCTTGTAAAGCCTTTTTTATCTTAGAAGGGCATGTGGGCAA<br>CTGTCTTTGACACATTGAAACCGCCTGTATGGTGGTGGATGTCT<br>TGAAGGTTGATTTGGACCTCATTTACTTGGGCAGATCCTCTATA<br>TATTCTGATAAT |
| STAT3-100 bp HA<br>(SEQ ID NO: 14) | GCAGCTTGACACACGGTACCTGGAGCAGCTCCATCAGCTCTA<br>CAGTGACAGCTTCCCAATGGAGCTGCGGCAGTTTCTGGCCCCT<br>TGGATTGAGAGTCAAGAATTCGATTGGTAAGTCCTTCTTAAGT<br>GACTCTCCAAATTGTTAGGTTTCAGTTTGAGTCAAGAGACATG<br>AACTCTTAATGTCATGCCTTGCTGTTCCATTAAAA |

TABLE 4

| Primers for EcoRI cleavage Assay | | | | |
|---|---|---|---|---|
| Gene | Forward Primer | Forward Primer Sequence | Reverse Primer | Reverse Primer Sequence |
| SERPINC1 | SERPINC1 F (SEQ ID NO: 15) | GAGGTAGTTGG GACACTCGATG AAG | SERPINC1 R (SEQ ID NO: 16) | TGCTGGGGAATGGGT CTCTCTGTGG |
| HPRT1 | HPRT1 F (SEQ ID NO: 17) | ATCGCTAGAGCC CAAGAAGTCAAG G | HPRT1 R (SEQ ID NO: 18) | TGACTAATGGGAACC ATCAGTCTGT |
| STAT3 | STAT3 F (SEQ ID NO: 19) | GCAGCAGATGCT GCTATGCT | STAT3 R (SEQ ID NO: 20) | TCACACACTTCTGGTA GATAATGGATTCTAGAA |

Definitions

To aid in understanding the invention, several terms are defined below.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "CRISPR" refers to Clustered Regularly Interspaced Short Palindromic Repeat bacterial adaptive immune system.

The terms "Cas" and "Cas endonuclease" generally refers to a CRISPR-associated endonuclease.

The term "Cas protein" generally refers to a wild-type protein, including a variant thereof, of a CRISPR-associated endonuclease (including the interchangeable terms Cas and Cas endonuclease).

The term "Cas nucleic acid" generally refers to a nucleic acid of a CRISPR-associated endonuclease, including a guide RNA, sgRNA, crRNA, or tracrRNA.

The terms "Cas9" and "CRISPR/Cas9" refer to the CRISPR-associated bacterial adaptive immune system of *Steptococcus pyogenes*. Examples of this system are disclosed in U.S. patent application Ser. Nos. 15/729,491 and 15/964,041, filed Oct. 10, 2017 and Apr. 26, 2018, respectively, the contents of which are incorporated by reference herein.

The term "variant," as that term modifies a protein (for example, ubiquitin), refers to a protein that includes at least one amino substitution of the reference, typically wild-type, protein amino acid sequence, additional amino acids (for example, such as an affinity tag or nuclear localization signal), or a combination thereof.

The term "polypeptide" refers to any linear or branched peptide comprising more than one amino acid. Polypeptide includes protein or fragment thereof or fusion thereof, provided such protein, fragment or fusion retains a useful biochemical or biological activity.

A fusion proteins typically includes extra amino acid information that is not native to the protein to which the extra amino acid information is covalently attached. Such extra amino acid information may include tags that enable purification or identification of the fusion protein. Such extra amino acid information may include peptides that enable the fusion proteins to be transported into cells and/or transported to specific locations within cells. Examples of tags for these purposes include the following: AviTag, which is a peptide allowing biotinylation by the enzyme BirA so the protein can be isolated by streptavidin (GLNDIFEAQKIEWHE; SEQ ID NO:21); Calmodulin-tag, which is a peptide bound by the protein calmodulin (KRRWKKNFIAVSAANRFK-KISSSGAL; SEQ ID NO:22); E-tag, which is a peptide recognized by an antibody (GAPVPYPDPLEPR; SEQ ID NO:23); FLAG-tag, which is a peptide recognized by an antibody (DYKDDDDK; SEQ ID NO:24); HA-tag, which is a peptide from hemagglutinin recognized by an antibody (YPYDVPDYA; SEQ ID NO:25); His-tag, which is typically 5-10 histidines bound by a nickel or cobalt chelate (e.g., HHHHHH; SEQ ID NO:26); Myc-tag, which is a peptide derived from c-myc recognized by an antibody (EQKLISEEDL; SEQ ID NO:27); NE-tag, which is a novel 18-amino-acid synthetic peptide (TKENPRSNQEESYDD-NES; SEQ ID NO:28) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, which is a peptide derived from Ribonuclease A (KETAAAKFERQHMDS; SEQ ID NO:29); SBP-tag, which is a peptide which binds to streptavidin; (MDEKTTGWRGGHVVEGLAGELEQL-RARLEHHPQGQREP; SEQ ID NO:30)); Softag 1, which is intended for mammalian expression (SLAEL-LNAGLGGS; SEQ ID NO:31); Softag 3, which is intended for prokaryotic expression (TQDPSRVG; SEQ ID NO:32); Strep-tag, which is a peptide which binds to streptavidin or the modified streptavidin called streptactin (Strep-tag II: WSHPQFEK; SEQ ID NO:33); TC tag, which is a tetracysteine tag that is recognized by FlAsH and ReAsH biarsenical compounds (CCPGCC; SEQ ID NO:34); V5 tag, which is a peptide recognized by an antibody (GKPIPN-PLLGLDST; SEQ ID NO:35); VSV-tag, a peptide recognized by an antibody (YTDIEMNRLGK; SEQ ID NO:36); Xpress tag (DLYDDDDK; SEQ ID NO:37); Isopeptag, which is a peptide which binds covalently to pilin-C protein (TDKDMTITFTNKKDAE; SEQ ID NO:38); SpyTag, which is a peptide which binds covalently to SpyCatcher protein (AHIVMVDAYKPTK; SEQ ID NO:39); SnoopTag, a peptide which binds covalently to SnoopCatcher protein (KLGDIEFIKVNK; SEQ ID NO:40); BCCP (Biotin Carboxyl Carrier Protein), which is a protein domain biotinylated by BirA to enable recognition by streptavidin; Glutathione-S-transferase-tag, which is a protein that binds to immobilized glutathione; Green fluorescent protein-tag, which is a protein which is spontaneously fluorescent and can be bound by antibodies; HaloTag, which is a mutated bacterial haloalkane dehalogenase that covalently attaches to a reactive haloalkane substrate to allow attachment to a wide variety of substrates; Maltose binding protein-tag, a protein which binds to amylose agarose; Nus-tag; Thioredoxin-tag; and Fc-tag, derived from immunoglobulin Fc domain, which allows dimerization and solubilization and can be used for purification on Protein-A Sepharose. Nuclear localization signals (NLS), such as those obtained from SV40, allow for proteins to be transported to the nucleus immediately upon entering the cell. Given that the native Cas9 protein is bacterial in origin and therefore does not naturally comprise a NLS motif, addition of one or more NLS motifs to the recombinant Cas9 protein is expected to show improved genome editing activity when used in eukaryotic cells where the target genomic DNA substrate resides in the nucleus. One skilled in the art would appreciate these various fusion tag technologies, as well as how to make and use fusion proteins that include them.

The term "tag-free" as that term modifies a polypeptide refers to a polypeptide lacking extra amino acid information that is not native to the polypeptide.

The terms "Ubiquitin" or "human Ubiquitin" refers to the wild-type Ubiquitin polypeptide amino acid sequence.

The terms "i53," i53 Ubiquitin," or "Ubiquitin i53" refers to a ubiquitin variant polypeptide amino acid sequence that lacks the carboxy terminal di-glycine of the wild-type Ubiquitin polypeptide and includes several amino acid substitutions (Q2L, I44A, Q49S, Q62L, E64D, T66K, L69P, and V70L) relative to the wild-type Ubiquitin polypeptide.

REFERENCES

1. Chapman, J. R., Taylor, M. R. & Boulton, S. J. Playing the end game: DNA double-strand break repair pathway choice. *Molecular cell* 47, 497-510 (2012).
2. Iwabuchi, K., Bartel, P. L., Li, B., Marraccino, R. & Fields, S. Two cellular proteins that bind to wild-type but not mutant p53. *Proceedings of the National Academy of Sciences of the United States of America* 91, 6098-6102 (1994).
3. Escribano-Díaz, C. et al. A cell cycle-dependent regulatory circuit composed of 53BP1-RIF1 and BRCA1-CtIP controls DNA repair pathway choice. *Molecular cell* 49, 872-883 (2013).
4. Feng, L., Fong, K. W., Wang, J., Wang, W. & Chen, J. RIF1 counteracts BRCA1-mediated end resection during DNA repair. *The Journal of biological chemistry* 288, 11135-11143 (2013).
5. Xie, A. et al. Distinct roles of chromatin-associated proteins MDC1 and 53BP1 in mammalian double-strand break repair. *Molecular cell* 28, 1045-1057 (2007).
6. Gaj, T., Sirk, S. J., Shui, S. L. & Liu, J. Genome-Editing Technologies: Principles and Applications. *Cold Spring Harbor perspectives in biology* 8 (2016).
7. Botuyan, M. V. et al. Structural basis for the methylation state-specific recognition of histone H4-K20 by 53BP1 and Crb2 in DNA repair. *Cell* 127, 1361-1373 (2006).
8. Charier, G. et al. The Tudor tandem of 53BP1: a new structural motif involved in DNA and RG-rich peptide binding. *Structure* (London, England: 1993) 12, 1551-1562 (2004).
9. Fradet-Turcotte, A. et al. 53BP1 is a reader of the DNA-damage-induced H2A Lys 15 ubiquitin mark. *Nature* 499, 50-54 (2013).
10. Mattiroli, F. et al. RNF168 ubiquitinates K13-15 on H2A/H2AX to drive DNA damage signaling. *Cell* 150, 1182-1195 (2012).
11. Canny, M. D. et al Inhibition of 53BP1 favors homology-dependent DNA repair and increases CRISPR-Cas9 genome-editing efficiency. *Nature biotechnology* 36, 95-102 (2018).
12. Dikic, I., Wakatsuki, S. & Walters, K. J. Ubiquitin-binding domains—from structures to functions. *Nature reviews. Molecular cell biology* 10, 659-671 (2009).
13. Davis, L. & Maizels, N. Two Distinct Pathways Support Gene Correction by Single-Stranded Donors at DNA Nicks. *Cell reports* 17, 1872-1881 (2016).
14. Verma, P. & Greenberg, R. A. Noncanonical views of homology-directed DNA repair. *Genes & development* 30, 1138-1154 (2016).
15. Roth, T. L. et al. Reprogramming human T cell function and specificity with non-viral genome targeting. *Nature* 559, 405-409 (2018).
16. Li, X. L. et al. Highly efficient genome editing via CRISPR-Cas9 in human pluripotent stem cells is achieved by transient BCL-XL overexpression. *Nucleic Acids Res* 46, 10195-10215 (2018).
17. Sun, L., Wu, J., Du, F., Chen, X. & Chen, Z. J. Cyclic GMP-AMP synthase is a cytosolic DNA sensor that activates the type I interferon pathway. *Science* 339, 786-791 (2013).
18. Dudek, A. M. & Porteus, M. H. Answered and Unanswered Questions in Early-Stage Viral Vector Transduction Biology and Innate Primary Cell Toxicity for Ex-Vivo Gene Editing. *Front Immunol* 12, 660302 (2021).
19. Yu, K. R., Natanson, H. & Dunbar, C. E. Gene Editing of Human Hematopoietic Stem and Progenitor Cells: Promise and Potential Hurdles. *Hum Gene Ther* 27, 729-740 (2016).
20. Eyquem, J. et al. Targeting a CAR to the TRAC locus with CRISPR/Cas9 enhances tumour rejection. *Nature* 543, 113-117 (2017).
21. Martin, R. M. et al. Highly Efficient and Marker-free Genome Editing of Human Pluripotent Stem Cells by CRISPR-Cas9 RNP and AAV6 Donor-Mediated Homologous Recombination. *Cell Stem Cell* 24, 821-828 e825 (2019).
22. Grimm, D. et al. In vitro and in vivo gene therapy vector evolution via multispecies interbreeding and retargeting of adeno-associated viruses. *J Virol* 82, 5887-5911 (2008).
23. Riesenberg, S. & Maricic, T. Targeting repair pathways with small molecules increases precise genome editing in pluripotent stem cells. *Nat Commun* 9, 2164 (2018).

24. Brault, J. et al. CRISPR-targeted MAGT1 insertion restores XMEN patient hematopoietic stem cells and lymphocytes. *Blood* 138, 2768-2780 (2021).
25. De Ravin, S. S. et al. Enhanced homology-directed repair for highly efficient gene editing in hematopoietic stem/progenitor cells. *Blood* 137, 2598-2608 (2021).
26. Sweeney, C. L. et al. Correction of X-CGD patient HSPCs by targeted CYBB cDNA insertion using CRISPR/Cas9 with 53BP1 inhibition for enhanced homology-directed repair. *Gene Ther* 28, 373-390 (2021).
27. Wienert, B. et al. Timed inhibition of CDC7 increases CRISPR-Cas9 mediated templated repair. *Nat Commun* 11, 2109 (2020).

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated nucleic acid sequence comprising a nucleic acid sequence encoding the tag-free ubiquitin polypeptide variant of SEQ ID NO: 2.

2. The isolated nucleic acid sequence of claim 1, comprising a nucleic acid sequence encoding the ubiquitin polypeptide variant of SEQ ID NO: 3.

3. An isolated tag-free polypeptide comprising SEQ ID NO: 2.

4. The isolated tag-free polypeptide of claim 3, wherein the tag-free polypeptide comprises SEQ ID NO: 3.

5. A method for improving homology directed repair (HDR) in a recipient cell, comprising: introducing a nucleic acid donor template and an isolated tag-free polypeptide comprising SEQ ID NO: 2 into the recipient cell.

6. The method of claim 5, wherein an adeno-associated virus vector is used to introduce the nucleic acid donor template.

7. The method of claim 5, wherein the isolated tag-free polypeptide comprises SEQ ID NO: 3.

* * * * *